United States Patent [19]

Dostert

[11] 3,985,895
[45] Oct. 12, 1976

[54] N,N-DIETHYL-N'-{DIBENZO[b,e]THIEPIN-11(6H)-YLIDENE}-1,3-PROPANEDIAMINE AND DERIVATIVES THEREOF

[75] Inventor: Philippe Dostert, Versailles, France

[73] Assignee: Hoffmann-La Roche Inc., Nutley, N.J.

[22] Filed: Mar. 14, 1975

[21] Appl. No.: 558,401

[30] Foreign Application Priority Data
Mar. 20, 1974 Switzerland.................. 3879/74
Feb. 11, 1975 Switzerland.................. 1648/75

[52] U.S. Cl................. 424/275; 260/327 B
[51] Int. Cl.²........................ C07D 337/12
[58] Field of Search.......... 260/327 B; 424/275

[56] References Cited
FOREIGN PATENTS OR APPLICATIONS
2,150,079  4/1972  Germany.................. 260/327 B Primary Examiner—Natalie Trousof
Assistant Examiner—C. M. S. Jaisle
Attorney, Agent, or Firm—Samuel L. Welt; Bernard S. Leon; William G. Isgro

[57] ABSTRACT

Dibenzo[b,e]thiepin derivatives of the formula

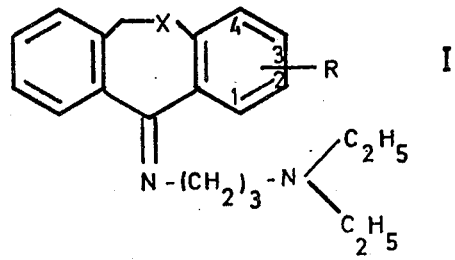

wherein X is sulfur or sulfonyl and R is hydrogen or methyl, are described. The compounds of formula I are useful as diuretic agents.

10 Claims, No Drawings

N,N-DIETHYL-N'-{DIBENZO[b,e]THIEPIN-11(6H)-YLIDENE}-1,3-PROPANEDIAMINE AND DERIVATIVES THEREOF

BRIEF SUMMARY OF THE INVENTION

The invention relates to tricyclic compounds of the formula

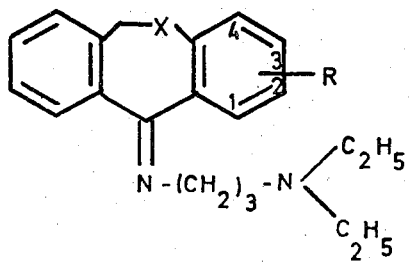

wherein X is sulfur or sulfonyl and R is hydrogen or methyl, and pharmaceutically acceptable acid addition salts thereof.

DETAILED DESCRIPTION OF THE INVENTION

The tricyclic compounds of the invention are characterized by the formula

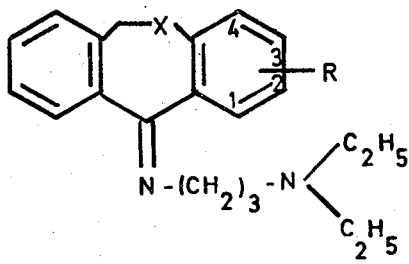

wherein X is sulfur or sulfonyl and R is hydrogen or methyl.

Exemplary of such compounds are:
N,N-diethyl-N'-{dibenzo[b,e]thiepin-11(6H)-ylidene}-1,3-propanediamine;
N,N-diethyl-N'-{2-methyl-dibenzo[b,e]thiepin-11(6H)-ylidene}-1,3-propanediamine;
N,N-diethyl-N'-{4-methyl-dibenzo[b,e]thiepin-11(6H)-ylidene}-1,3-propanediamine;
N,N-diethyl-N'-{dibenzo[b,e]thiepin-11(6H)-ylidene}-1,3-propanediamine-5,5-dioxide;
and pharmaceutically acceptable acid addition salts thereof.

In a preferred aspect, the invention relates to N,N-diethyl-N'-{dibenzo-[b,e]thiepin-11(6H)-ylidene}=1,3-propanediamine and its pharmaceutically acceptable acid addition salts.

The compounds of formula I and their acid addition salts are prepared by:
a. reacting a ketone of the formula

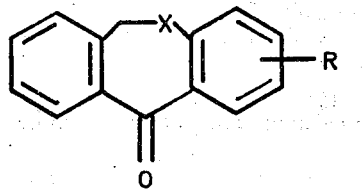

wherein X and R are as hereinbefore described, with N,N-diethyl-1,3-propanediamine in the presence of a dehydrating agent; or b. to prepare a compound of formula I wherein X is sulfur, reacting a compound of the formula

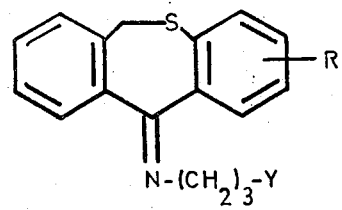

wherein X and R are as hereinbefore described and Y is a leaving group,
with diethylamine; or c. deoxygenating an N'-oxide of the formula

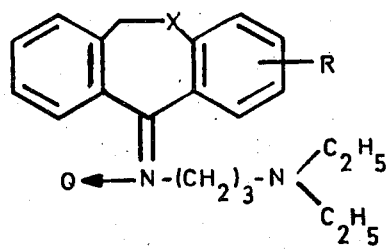

wherein X and R are as hereinbefore described; or d. to prepare a compound of formula I wherein X is sulfur, dehydrogenating an amine of the formula

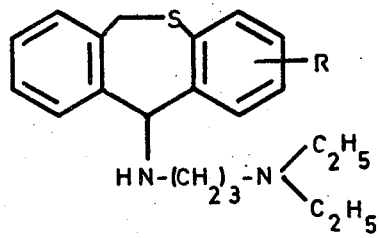

wherein R is as hereinbefore described; or e. ethylating a compound of the formula

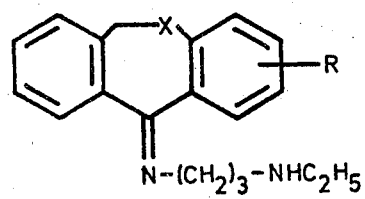

wherein X and R are as hereinbefore described, and, if desired, converting a compound of formula I that is obtained into a pharmaceutically acceptable acid addition salt.

The ketone starting materials of formula II are known and can be prepared in a known manner.

As the dehydrating agent in process embodiment (a) there can be used a Lewis acid, preferably a halide of an element from group III, IV, V or VIII of the periodic system. Examples of such halides are:

with an element from Group III of the periodic system: boron trifluoride, boron trichloride and aluminum trichloride;

with an element from group IV of the periodic system: titanium tetrachloride, germanium tetrachloride, zinc tetrachloride and zirconium tetrachloride;

with an element from group V of the periodic system: arsenic trichloride, antimony trichloride and antimony pentachloride;

with an element from group VIII of the periodic system: ferric chloride.

Preferred of the aforementioned Lewis acids are titanium tetrachloride and antimony trichloride.

The reaction of a ketone of formula II with N,N-diethyl-1,3-propanediamine is conveniently carried out in a solvent with the selected dehydrating agent at a temperature in the range of from about room temperature to the boiling point of the reaction mixture.

The choice of solvent is determined by the solubility of the ketone starting material of formula II utilized in the reaction. Suitable solvents include, for example, ethers, such as, diethyl ether, tetrahydrofuran or dioxane; cyclic hydrocarbons, such as, cyclohexane, benzene, toluene or mesitylene; and chlorinated hydrocarbons, such as, methylene chloride. The Lewis acid used as the dehydrating agent is conveniently used in solution. Conveniently, in the same solvent as used for the ketone. If, for example, titanium tetrachloride is used as the dehydrating agent, then diethyl ether, benzene or toluene is preferably used as the solvent.

The oxide corresponding to the Lewis acid which is formed during the reaction is separated. If desired, said oxide can be converted back into the halide which can again be used as the dehydrating agent.

The leaving group denoted by Y in the compounds of formula III is preferably a halogen, for example, chlorine or bromine; a lower alkanesulfonyloxy, for example, methanesulfonyloxy (mesyloxy); or a benzenesulfonyloxy which may be substituted by lower alkyl or halogen, for example, benzenesulfonyloxy, p-toluenesulfonyloxy (tosyloxy) or p-bromobenzenesulfonyloxy (brosyloxy).

The starting materials of formula III are known compounds and can be prepared in a known manner. For example, they can be prepared by condensing a corresponding, optionally ring-substituted, tricyclic ketone of formula II with 3-amino-1-propanol, whereby water cleaves and subsequently halogenating, mesylating or tosylating the resulting N-(3-hydroxypropyl)-imine, the latter step can be carried out, for instance, by reacting the aforementioned imine with, for example, p-toluenesulfonyl chloride, conveniently in an organic solvent, for example, a hydrocarbon, such as, benzene, at room temperature.

A compound of formula III, for example, one in which Y is halogen or mesyloxy or tosyloxy, can readily be reacted with diethylamine in accordance with process embodiment (b). If desired, this reaction can be carried out in the presence of an acid-binding agent, for example, potassium carbonate or sodium carbonate, for instance, in an organic solvent, for example, a lower alkanol, such as, ethanol; or a cyclic hydrocarbon such as toluene or xylene. An excess of diethylamine may be used to serve as the acid-binding agent or solvent and, in such a case, the reaction is advantageously carried out under pressure. The reaction of a compound of formula III with diethylamine is preferably carried out at a temperature in the range of from about room temperature to the boiling point of the reaction mixture.

The N'-oxide starting materials of formula IV are known and can be prepared in a known manner.

The deoxygenation of an N'-oxide of formula IV according to process embodiment (c) to give a compound of formula I is carried out in a known manner with the aid of a trivalent reducing phosphorus compound, for example, a tri(lower alkyl)phosphite, such as, triethylphosphite; a tris[di(lower alkylamino)]phosphine, such as, tris(dimethylamino)-phosphine; triphenylphosphine; or a phosphorus trihalide, such as, phosphorus trichloride or phosphorus tribromide, conveniently in an organic solvent, for example, a cyclic hydrocarbon, such as, benzene or toluene; a halogenated hydrocarbon, such as, methylene chloride or chloroform; or diethyleneglycol dimethyl ether, at a temperature in the range of from about room temperature to the boiling point of the reaction mixture.

The amine starting materials of formula V are known compounds and can be dehydrogenated according to process embodiment (d) to give compounds of formula I as hereinafter described. For instance, an amine of formula V is dissolved in an organic solvent, for example, a halogenated hydrocarbon, such as, methylene chloride or chloroform; or a cyclic hydrocarbon, such as, benzene or toluene, and is treated at a temperature in the range of from about room temperature to the boiling point of the mixture with an alkali hypohalite, preferably, sodium hypochlorite, conveniently in the presence of a solvent, for example, tetrahydrofuran or dioxane, at a temperature of from about 0° C. to about 100° C., preferably at a temperature below room temperature.

The dehydrogenation proceeds through a halide intermediate of the formula

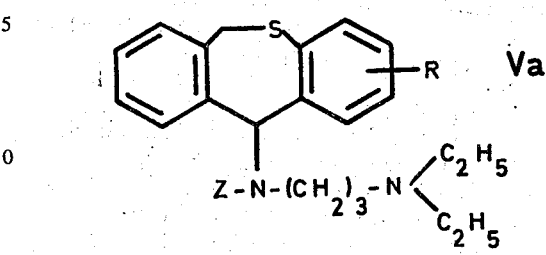

wherein R is as hereinbefore described and Z is halogen, which cannot be isolated and which is dehydrohalogenated as it forms under the said conditions.

The secondary amines of formula VI employed according to process embodiment (e) can be prepared from a ketone of formula II and N-ethyl-1,3-propanediamine in an analogous manner to the preparation of the end products of formula I from ketones of formula II and N,N-diethyl-1,3-propanediamine described above.

The ethylation of the secondary amines of formula VI according to process embodiment (e) is carried out in a known manner by treating the secondary amines of formula VI with an ethylating agent, for example, with a compound of the formula

   VII wherein Y is a leaving group.

The leaving group Y has the same significance as described above in formula III. According to another embodiment, diethylsulfate is used as the ethylating agent. The ethylating process is preferably carried out in an inert organic solvent, for example, in a lower aliphatic ketone, such as, acetone or methyl ethyl ketone; in an ether, such as, diethyl ether, tetrahydrofuran or dioxane; in a chlorinated lower aliphatic hydrocarbon, such as, chloroform or methylene chloride; or in an aromatic hydrocarbon, such as, benzene or toluene. The reaction temperature is not critical but conveniently is in the range of between about room temperature and the boiling point of the reaction mixture.

The compounds of formula I form mono- or di-acid addition salts and such salts are also within the scope of this invention. These salts are preferably manufactured in a solvent by treating the free base with an appropriate acid. Depending on the molar ratio between the free base and the acid there is obtained (because of the two nitrogen atoms in the side chain of the free base) a salt containing one or two moles of acid per mole of base (mono- or di-salt). The compounds of formula I form pharmaceutically acceptable addition salts with, for example, both pharmaceutically acceptable organic and inorganic acids, for example, hydrobromic acid, oxalic acid, trifluoroacetic acid, ethanesulfonic acid, acetic acid, succinic acid, formic acid, methanesulfonic acid, p-toluenesulfonic acid, hydrochloric acid, phosphoric acid, sulfuric acid and the like.

The compounds of formula I have a relatively good solubility in dimethylsulfoxide, dimethylformamide, chlorinated hydrocarbons, such as, chloroform or methylene chloride; aromatic hydrocarbons, such as, benzene or toluene; ethers, such as, diethyl ether or tetrahydrofuran; and lower alkanols, such as, methanol or ethanol, and are relatively insoluble in water.

The pharmaceutically acceptable acid addition salts of the compounds of formula I are, in part, crystalline solid substances. Such salts have a good solubility in dimethylsulfoxide, dimethylformamide and alkanols, such as, methanol or ethanol, and, in part, in chloroform, methylene chloride and water. Furthermore, they are relatively insoluble in benzene, diethyl ether and petroleum ether.

The compounds of formula I and their pharmaceutically acceptable acid addition salts have diuretic activity and are therefore useful as diuretic agents. The diuretic activity of the compounds of formula I can be demonstrated in warm-blooded animals by way of the following test.

The test is carried out on conscious, episiotomized dogs (8.6–10.6 kg.). Food is withdrawn from the test animals on the eve of the test, but tap water is given ad libitum until the beginning of the test. On the test day, the urinary bladder is catheterized.

Initially, 5 ml/kg. of water with a sodium chloride content of 0.9% is administered per os to the test animals. Two hours thereafter, the substance to be tested is administered in gelatin capsules to a test group, while empty capsules are administered to a control group. Water with a sodium chloride content of 0.9% is administered simultaneously to the two groups in an amount which corresponds to the urine volume secreted before administration of the gelatin capsules. The urine is collected over a period of six hours at hourly intervals, measured and analyzed for sodium and potassium ions. The individual hourly values (ml/kg/6 hours or milliequivalent/kg/6 hours) are added together and compared with the corresponding six-hourly secretions of the control group. The absolute values are calculated in relative values, the controls equalling 100 in each case. Utilizing this procedure, when 4 mg/kg. of N,N-diethyl-N'-{dibenzo[b,e]thiepin-11(6H)-ylidene}-1,3-propanediamine oxalate are administered, there is obtained a urine secretion of 408%, a sodium secretion of 481% and a potassium secretion of 125% as compared to the controls (100%), and when 2 mg/kg. of N,N-diethyl-N'-{4-methyl-dibenzo[b,e]thiepin-11(6H)-ylidene}-1,3-propanediamine oxalate are administered, there is obtained a urine secretion of 279%, a sodium secretion of 325% and a potassium secretion of 122% as compared to the controls.

The amount of a compound of formula I administered to a warm-blooded animal varies within a wide range according to the compound used. In general, the daily dosage in the case of oral administration comprises from about 50 mg. to about 150 mg.

The compounds of formula I and their pharmaceutically acceptable acid addition salts can be used as medicaments in the form of pharmaceutical preparations which contain them in combination with a compatible pharmaceutical carrier. Such carrier can be an organic or inorganic inert carrier suitable for enteral administration, for example, gelatin, gum arabic, lactose, starch, vegetable oils, polyalkyleneglycols, or the like. The pharmaceutical preparations can be made up, for example, as tablets, dragees or capsules. The pharmaceutical preparations may contain adjuvants, such as, preservatives, stabilizers, wetting agents, emulsifiers or salts for varying the osmotic pressure. Such preparations may also contain other therapeutically active substances.

The following Examples further illustrate the invention. All temperatures are stated in degrees Centigrade, unless otherwise mentioned.

EXAMPLE 1

Preparation of N,N-diethyl-N'-{dibenzo[b,e]thiepin-11(6H)-ylidene}-1,3-propanediamine, N,N-diethyl-N'-{dibenzo[b,e]thiepin-11(6H)-ylidene}-1,3-propanediamine diethanesulfonate and N,N-diethyl-N'-{dibenzo[b,e]thiepin-11(6H)-ylidene}-1,3-propanediamine monotrifluoroacetate 113 G. of dibenzo[b,e]thiepin-11(6H)-one are dissolved in 2.5 liters of absolute toluene while stirring at room temperature. After the addition of 585 g. of N,N-diethyl-1,3-propanediamine, the solution is cooled to 0° C. and treated dropwise with 110 ml. of titanium tetrachloride. The mixture is stirred at room temperature for 18 hours, then cooled to 0° C., hydrolyzed with 3 liters of water and filtered. The filter cake is washed twice with 300 ml. of ether. The organic phase is separated and the aqueous solution extracted with ether. The combined organic extracts are washed with a saturated aqueous sodium chloride solution, dried over sodium sulfate and evaporated under reduced pressure. The residual N,N-diethyl-N'-{dibenzo[b,e]thiepin- 11(6H)-ylidene}-1,3-propanediamine (165.1 g.; isomer mixture) is taken up in acetone and treated with a solution of 113 g. of ethanesulfonic acid (95%, 5% H₂O) in 100 ml. of acetone. The N,N-diethyl-N'-{dibenzo[b,e]thiepin-11(6H)-ylidene}-1,3-propanediamine diethanesulfonate (226 g.), which separates in crystalline form, melts at 177°–179° C. after recrystallization from acetone/methanol. The corresponding N,N-diethyl-N'-{dibenzo[b,e]thiepin-11(6H)-ylidene}-1,3-propanediamine monotrifluoroacetate melts at 118°–119° C.

EXAMPLE 2

In an analogous manner,
from 4-methyl-dibenzo[b,e]thiepin-11(6H)-one and N,N-diethyl-1,3-propanediamine, there can be prepared N,N-diethyl-N'-{4-methyl-dibenzo[b,e]thiepin-11(6H)-ylidene}-1,3-propanediamine of melting point 174°–176° C. (oxalate);

from dibenzo[b,e]thiepin-11(6H)-one-5,5-dioxide and N,N-diethyl-1,3-propanediamine, there can be prepared N,N-diethyl-N'-{dibenzo[b,e]thiepin-11(6H)-ylidene}-1,3-propanediamine-5,5-dioxide of melting point 114°–117° C. (oxalate); and from 2-methyl-dibenzo[b,e]thiepin-11(6H)-one and N,N-diethyl-1,3-propanediamine, there can be prepared N,N-diethyl-N'-{2-methyl-dibenzo[b,e]thiepin-11(6H)-ylidene}-1,3propanediamine of melting point 154°–157° C. (oxolate).

EXAMPLE 3

Preparation of
N,N-diethyl-N'-{dibenzo[b,e]thiepin-11(6H)-ylidene}-1,3-propanediamine 8.6 G. of crude 3-{(dibenzo[b,e]thiepin-11(6H)-yliden)-amino}-propyl tosylate are heated in an autoclave to 70° C. for 16 hours with 40 ml. of diethylamine. After cooling, the mixture is evaporated under reduced pressure and the residue dissolved in ether. The ether solution is extracted with 3N aqueous hydrochloric acid. The aqueous extract is made alkaline with sodium carbonate and extracted with ether. The organic phase is dried over sodium sulfate and evaporated under reduced pressure. After chromatographic purification over aluminum oxide using toluene for the elution, there is obtained N,N-diethyl-N'-{dibenzo[b,e]thiepin-11(6H)-ylidene}-1,3-propanediamine which is identical with the compound obtained according to Example 1.

The 3-{(dibenzo[b,e]thiepin-11(6H)-yliden)-amino}-propyl tosylate used as the starting material can be prepared as follows:

30.0 G. of dibenzo[b,e]thiepin-11(6H)-one are heated to 180° C. with 300 ml. of 3-amino-1-propanol. The water formed and the excess amine are distilled off for 2 hours and the residue is then cooled, diluted with methylene chloride and washed several times with distilled water. The organic phase is dried over sodium sulfate and evaporated. After chromatographic purification over silica gel using toluene for the elution, there is obtained 3-{(dibenzo[b,e]-thiepin-11(6H)-yliden)-amino}-1-propanol.

10.0 G. of 3-{(dibenzo[b,e]thiepin-11(6H)-yliden)-amino}-1-propanol in 30 ml. of absolute pyridine are treated at 0° C. within 1 hour with 9.0 g. of p-toluenesulfonyl chloride. The solution is stirred at 0° C. for 1 hour and subsequently left to stand at 0° C. for 16 hours. The mixture is then diluted with methylene chloride and treated with water. The organic phase is washed with aqueous sodium bicarbonate solution, dried over sodium sulfate and evaporated under reduced pressure. There is obtained crude 3-{(dibenzo[b,e]thiepin-11(6H)-yliden)-amino}-propyl tosylate which is used in the reaction described in the first paragraph of this Example without further purification.

EXAMPLE 4

Preparation of
N,N-diethyl-N'-{dibenzo[b,e]thiepin-11(6H)-ylidene}-1,3-propanediamine 1.0 G. of phosphorus trichloride in 20 ml. of toluene is treated dropwise with 1.4 g. of N,N-diethyl-N'-{dibenzo[b,e]thiepin-11(6H)-ylidene}-1,3-propanediamine-N'-oxide in 10 ml. of absolute toluene. The mixture is stirred at room temperature for 30 minutes and then cautiously made alkaline with an aqueous sodium carbonate solution. The mixture is then extracted with ether. The organic phase is dried over sodium sulfate and evaporated under reduced pressure. The residue is purified by a two-fold chromatography over aluminum oxide using toluene for the elution. There is thus obtained N,N-diethyl-N'-{dibenzo[b,e]thiepin-11(6H)-ylidene}-1,3-propanediamine which is identical with the compound obtained according to Example 1.

The N,N-diethyl-N'-{dibenzo[b,e]thiepin-11(6H)-ylidene}-1,3-propanediamine-N'-oxide used as the starting material can be prepared as follows:

19.7 G. of dibenzo[b,e]thiepin-11(6H)-one and 14.6 g. of hydroxylamine hydrochloride in 350 ml. of pyridine are stirred under reflux conditions for 16 hours. After the addition of a further 7.3 g. of hydroxylamine hydrochloride, the mixture is stirred for a further 5 hours under reflux conditions. The mixture is evaporated and purified by chromatography over aluminum oxide using chloroform and chloroform/methanol (93:3) for the elution. The purified product is recrystallized from acetone. There is obtained dibenzo[b,e]thiepin-11(6H)-one-oxime of melting point 241°–243° C.

1.65 G. of sodium in 60 ml. of absolute ethanol are treated dropwise with 11.4 g. of dibenzo[b,e]thiepin-11(6H)-one-oxime in 60 ml. of absolute ethanol. The mixture is stirred at 50° C. for 3 hours and then cooled to 5°–10° C. The mixture is then treated dropwise with 15.3 g. of 3-diethylamino-propyl chloride, stirred at 50° C. for 16 hours and subsequently evaporated under reduced pressure. The residue is dissolved in chloroform, washed with water, dried over sodium sulfate and evaporated under reduced pressure. The resulting residue is purified by chromatography over aluminum oxide using chloroform for the elution. A by-product is first eluted and there is subsequently eluted the desired N,N-diethyl-N'-{dibenzo[b,e]thiepin-11(6H)-ylidene}-1,3-propanediamine-N'-oxide which is used directly in the process described in the first paragraph of this Example.

EXAMPLE 5

Preparation of
N,N-diethyl-N'-{dibenzo[b,e]thiepin-11(6H)-ylidene}-1,3-propanediamine-5,5-dioxide 0.6 G. of phosphorus trichloride in 30 ml. of absolute toluene is treated dropwise with 0.6 g. of N,N-diethyl-N'-{dibenzo[b,e]thiepin-11(6H)-ylidene}-1,3- propanediamine-N',5,5-trioxide in 20 ml. of absolute toluene. The mixture is stirred at 60°–70° C. for 1 hour, then cooled to room temperature and cautiously treated with aqueous sodium carbonate solution. After equilibration of the two phases, the aqueous phase is separated and extracted with methylene chloride. The methylene chloride extract is dried over sodium sulfate and evaporated under reduced pressure. The residue is purified by chromatography over aluminum oxide using chloroform for the elution. There is obtained N,N-diethyl-N'-{dibenzo[b,e]thiepin-11(6H)-ylidene}-1,3-propanediamine-5,5-dioxide which is identical with the second end product mentioned in Example 2.

The N,N-diethyl-N'-{dibenzo[b,e]thiepin-11(6H)-ylidene}-1,3-propanediamine-N',5,5-trioxide used as the starting material can be prepared as follows:

11.3 G. of dibenzo[b,e]thiepin-11(6H)-one-5,5-dioxide and 7.3 g. of hydroxylamine hydrochloride are heated under reflux conditions overnight in 170 ml. of absolute pyridine. The mixture is evaporated, treated with some water and extracted with methylene chloride. The methylene chloride extract is dried over sodium sulfate and evaporated. The resulting dibenzo[b,e]thiepin-11(6H)-one-oxime-5,5-dioxide is recrystallized from acetone and then melts at 204°–206° C.

1.65 G. of sodium in 60 ml. of absolute ethanol are treated dropwise with 12.8 g. of dibenzo[b,e]thiepin-11(6H)-one-oxime-5,5-dioxide in 60 ml. of absolute ethanol. The mixture is stirred at 50° C. for 3 hours, then cooled to 5° C. and treated dropwise with 15.3 g. of 3-diethylamino-propyl chloride. The mixture is stirred at 50° C. for 16 hours and then evaporated under reduced pressure. The residue is taken up in methylene chloride and extracted with 3N aqueous hydrochloric acid. The aqueous extract is made alkaline with sodium carbonate and extracted with methylene chloride. The organic phase is dried over sodium sulfate and evaporated under reduced pressure. The residue is purified by chromatography over aluminum oxide using chloroform/triethylamine (99:1) for the elution. A by-product is first eluted and there is subsequently eluted the desired N,N-diethyl-N'-{dibenzo[b,e]thiepin-11(6H)-ylidene}-1,3-propanediamine-N',5,5-trioxide which can be used directly in the process described in the first paragraph of this Example.

EXAMPLE 6

Preparation of N,N-diethyl-N'-{dibenzo[b,e]thiepin-11(6H)-ylidene}-1,3-propanediamine oxalate 2.3 G. of N,N-diethyl-N'-{6,11-dihydro-dibenzo[b,e]thiepin-11-yl}-1,3-propanediamine are dissolved in 50 ml. of absolute tetrahydrofuran and treated dropwise, while stirring, with 6 ml. of 14% aqueous sodium hypochlorite solution. The mixture is stirred at 40°–50° C. for 4 hours, cooled and mixed with 100 ml. of water. The organic phase is extracted with ether. The ether extract is dried over sodium sulfate and evaporated under reduced pressure. The residue is purified by chromatography over aluminum oxide using toluene for the elution. There is obtained N,N-diethyl-N'-{dibenzo[b,e]thiepin-11(6H)-ylidene}-1,3-propanediamine which is taken up in acetone and treated with a solution of 0.4 g. of oxalic acid in 10 ml. of absolute acetone. There is thus obtained N,N-diethyl-N'-{dibenzo[b,e]thiepin-11(6H)-ylidene}-1,3-propanediamine oxalate of melting point 130°–133° C.

The N,N-diethyl-N'-{6,11-dihydro-dibenzo[b,e]thiepin-11-yl}-1,3-propanediamine used as the starting material can be prepared as follows:

26.3 G. of dibenzo[b,e]thiepin-11(6H)-one in 600 ml. of ethanol are treated dropwise within 20 minutes under reflux conditions with 15.6 g. of sodium borohydride and 0.3 g. of sodium hydroxide in 65 ml. of water. The mixture is heated under reflux conditions for 3 hours. The mixture is then evaporated, treated with water and extracted with toluene. The organic phase is dried over sodium sulfate and evaporated. There is thus obtained 6,11-dihydro-dibenzo-[b,e]thiepin-11-ol of melting point 107°–109° C.

19.5 G. of 6,11-dihydro-dibenzo[b,e]thiepin-11-ol, 25 ml. of thionyl chloride and 180 ml. of absolute benzene are heated under reflux conditions for 2 hours. The mixture is evaporated, treated several times with absolute benzene and then evaporated. The crude 11-chloro-6,11-dihydro-dibenzo[b,e]thiepin obtained as the residue is used without further purification.

17.8 G. of crude 11-chloro-6,11-dihydro-dibenzo[b,e]thiepine, 18.8 g. of potassium carbonate, 1.0 g. of potassium iodide, 24 g. of N,N-diethyl-1,3-propanediamine and 400 ml. of absolute acetone are heated under reflux conditions for 6 hours. The mixture is evaporated, treated with water and extracted with ether. The organic phase is extracted with 3N aqueous hydrochloric acid, the aqueous phase made alkaline with sodium carbonate and extracted with ether. The ether extract is dried over sodium sulfate and evaporated. The resulting crude N,N-diethyl-N'-{6,11-dihydro-dibenzo[b,e]thiepin-11-yl}-1,3-propanediamine is purified by chromatography over aluminum oxide using toluene for the elution and is used directly in the process described in the first paragraph of this Example.

EXAMPLE 7

Preparation of N,N-diethyl-N'-{dibenzo[b,e]thiepin-11(6H)-yliden}-1,3-propanediamine 4.6 G. of N-ethyl-N'-{dibenzo[b,e]thiepin-11(6H)-yliden}-1,3-propanediamine, 4.5 g. of ethyl iodide, 4.5 g. of potassium carbonate and 0.1 g. of potassium iodide are heated for 3 hours in 80 ml. of absolute acetone. The reaction mixture is diluted with water and extracted with ether. The ether solution is extracted with 3N aqueous hydrochloric acid. The aqueous extract is made alkaline with sodium carbonate and extracted with ether. The organic phase is dried over sodium sulfate and evaporated under reduced pressure. The resulting N,N-diethyl-N'-{dibenzo[b,e]thiepin-11(6H)-yliden}-1,3-propanediamine can be purified by chromatography over aluminum oxide using toluene. The resulting compound is identical with the product mentioned in Example 1.

The N-ethyl-N'-{dibenzo[b,e]thiepin-11(6H)-yliden}-1,3-propanediamine used as the starting material can be prepared as follows:

9.1 g. of dibenzo[b,e]thiepin-11(6H)-one are mixed, while stirring, with 40 g. of N-ethyl-1,3-propanediamine and 250 ml. of absolute toluene and treated dropwise at 0° C. with 8.8 ml. of titanium tetrachloride. The reaction mixture is stirred at room temperature for 18 hours, then cooled and hydrolyzed with 250 ml. of water. The resulting suspension is filtered through diatomaceous earth and the aqueous phase is extracted with toluene. The combined toluene extracts are dried over sodium sulfate and evaporated under reduced pressure. Raw N-ethyl-N'-{dibenzo[b,e]thiepin-11(6H)-ylidene}-1,3-propanediamine is obtained which can be used directly in the above reaction.

EXAMPLE 8

Preparation of N,N-diethyl-N'-{dibenzo[b,e]thiepin-11(6H)-ylidene}-1,3-propanediamine-5,5-dioxide In the manner described in Example 7, N,N-diethyl-N'-{dibenzo[b,e]thiepin-11(6H)-ylidene}-1,3-propanediamine-5,5-dioxide is obtained from N-ethyl-N'-{dibenzo[b,e]thiepin-11(6H)-ylidene}-1,3-propanediamine-5,5-dioxide. The resulting compound is identical with the second end product mentioned in Example 2.

The above-mentioned starting material can be prepared in the same manner as described in Example 7 from dibenzo[b,e]thiepin-11(6H)-one-5,5-dioxide and N-ethyl-1,3-propanediamine.

The following Examples illustrate typical pharmaceutical preparations containing the dibenzo[b,e]thiepin derivatives provided by the present invention:

EXAMPLE A

Soft gelatin capsules containing the following ingredients are prepared:

| | |
|---|---|
| N,N-diethyl-N'- {dibenzo[b,e]thiepin-11-(6H)-ylidene} -1,3-propanediamine | 25 mg. |
| Polyethyleneglycol (average molecular weight 400) or Carbowax | 225 mg. |
| | 250 mg. |

The ingredients are homogeneously mixed and filled into soft gelatin capsules.

EXAMPLE B

Tablets containing the following ingredients are prepared:

| | |
|---|---|
| N,N-diethyl-N'- {dibenzo[b,e]thiepin-11(6H)-ylidene} 1,3-propanediamine trifluoroacetate | 10 mg. |
| Silicic acid | 25 mg. |
| Lactose | 115 mg. |
| Maize starch | 50 mg. |
| Calcium stearate | 10 mg. |
| | 210 mg. |

The N,N-diethyl-N'-{dibenzo[b,e]thiepin-11(6H)-ylidene}-1,3-propanediamine is mixed well with the remaining ingredients, granulated and pressed to tablets.

EXAMPLE C

Dragees of the following compositions are prepared:

| Nucleus: | |
|---|---|
| N,N-diethyl-N'- {dibenzo[b,e]thiepin-11(6H)-ylidene }-1,3-propanediamine trifluoroacetate | 50 mg. |
| Mannitol | 80 mg. |
| Talc | 5 mg. |
| Maize starch | 15 mg. |
| Nucleus Weight: | 150 mg. |

| Coating mass: | | |
|---|---|---|
| Sugar 90% | | |
| Rice starch 5% | Dragee Weight: | 150 mg. |
| Talc 5% | | 300 mg. |

The N,N-diethyl-N'-{dibenzo[b,e]thiepin-11(6H)-ylidene}-1,3-propanediamine trifluoroacetate is mixed with the mannitol and passed through a No. 5 sieve (mesh size ca. 0.23 mm.). The maize starch is boiled with water to a 10% paste. The powder mixture is homogeneously ground with this paste. The slightly moist mass is granulated using a No. 3 sieve (mesh size ca. 1.0 mm.). The granulate is dried and mixed with the talc. The mixture obtained is pressed to biconvex nuclei weighing 150 mg. The nuclei have a diameter of approximately 8.0 mm. They are then coated with sugar up to a final weight of 300 mg. using a sugar syrup according to known techniques.

I claim:
1. A compound of the formula

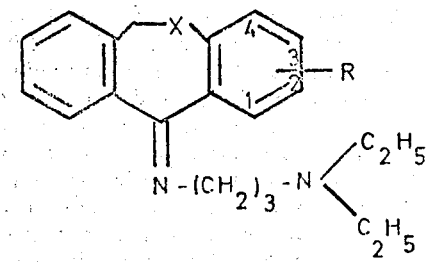

wherein
X is sulfur or sulfonyl and R is hydrogen or methyl, or a pharmaceutically acceptable acid addition salt thereof.

2. A compound in accordance with claim 1, wherein X is sulfur.

3. A compound in accordance with claim 1, wherein X is sulfonyl.

4. A compound in accordance with claim 2, i.e., N,N-diethyl-N'-{dibenzo[b,e]thiepin-11(6H)-ylidene}-1,3-propanediamine or a pharmaceutically acceptable acid addition salt thereof.

5. A compound in accordance with claim 2, i.e., N,N-diethyl-N'-{dibenzo[b,e]thiepin-11(6H)-ylidene}-1,3-propanediamine.

6. A compound in accordance with claim 2, i.e., N,N-diethyl-N'-{2-methyl-dibenzo[b,e]thiepin-11(6H)-ylidene}-1,3-propanediamine or a pharmaceutically acceptable acid addition salt thereof.

7. A compound in accordance with claim 2, i.e., N,N-diethyl-N'-{4-methyl-dibenzo[b,e]thiepin-11(6H)-ylidene}-1,3-propanediamine or a pharmaceutically acceptable acid addition salt thereof.

8. A compound in accordance with claim 3, i.e., N,N-diethyl-N'-{dibenzo[b,e]thiepin-11(6H)-ylidene}-1,3propanediamine-5,5-dioxide or a pharmaceutically acceptable acid addition salt thereof.

9. A composition having diuretic properties comprising a diuretically effective amount of a compound of the formula

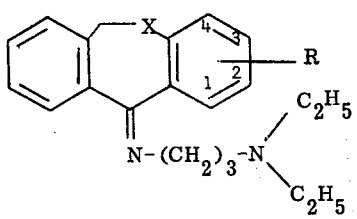

wherein X is sulfur or sulfonyl and R is hydrogen or methyl, or a pharmaceutically acceptable acid addition salt thereof and a carrier.

10. A method of increasing the passage of urine in a warm-blooded animal in need of diuresis which comprises administering to said warm-blooded animal a diuretically effective amount of a compound of the formula

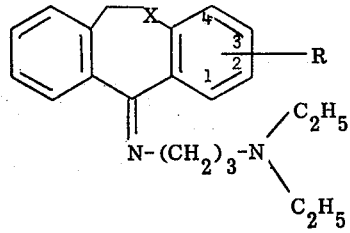

wherin X is sulfur or sulfonyl and R is hydrogen or methyl, or a pharmaceutically acceptable acid addition salt thereof.

* * * * *